US009453057B2

(12) United States Patent
Johnson et al.

(10) Patent No.: US 9,453,057 B2
(45) Date of Patent: Sep. 27, 2016

(54) **PLASMID-ENCODED NEUROTOXIN GENES IN *CLOSTRIDIUM BOTULINUM* SEROTYPE A SUBTYPES**

(71) Applicant: Wisconsin Alumni Research Foundation, Madison, WI (US)

(72) Inventors: Eric A. Johnson, Madison, WI (US); Kristin M. Marshall, Plainfield, IL (US); Sabine Pellett, Madison, WI (US); Marite Bradshaw, Madison, WI (US)

(73) Assignee: Wisconsin Alumni Research Foundation, Madison, WI (US)

( * ) Notice: Subject to any disclaimer, the term of this patent is extended or adjusted under 35 U.S.C. 154(b) by 0 days.

(21) Appl. No.: 13/800,997

(22) Filed: Mar. 13, 2013

(65) Prior Publication Data

US 2014/0065668 A1 Mar. 6, 2014

Related U.S. Application Data

(63) Continuation of application No. 12/664,800, filed as application No. PCT/US2008/068532 on Jun. 27, 2008, now Pat. No. 8,435,759.

(60) Provisional application No. 60/947,090, filed on Jun. 29, 2007.

(51) Int. Cl.
*C07K 14/33* (2006.01)
*C12N 15/74* (2006.01)

(52) U.S. Cl.
CPC .............. *C07K 14/33* (2013.01); *C12N 15/74* (2013.01)

(58) Field of Classification Search
CPC ............................. C07K 14/33; C12N 15/74
See application file for complete search history.

(56) References Cited

U.S. PATENT DOCUMENTS

| | | |
|---|---|---|
| 5,955,368 A | 9/1999 | Johnson et al. |
| 8,435,759 B2 | 5/2013 | Johnson et al. |

OTHER PUBLICATIONS

Arndt, et al., A Structural Perspective of the Sequence Variability Within Botulinum Neurotoxin Subtypes A1-A4, J. Mol. Biol., 2006, 362:733-742.
Arnon, et al., Botulinum Toxin as a Biological Weapon, Medical and Public Health Management, JAMA, 2001, 285 (8):1059-1070.
Beverley, et al., Characterization of the 'Unusual' Mobility of Large Circular DNAs in Pulsed Field-Gradient Electrophoresis, Nucleic Acids Research, 1988, 16(3):925-939.
Bradshaw, et al., Regulation of Neurotoxin Complex Expression in Clostridium Botulinum Strains 62A, Hall A-hyper, and NCTC 2916, Anaerobe, 2004, 10:321-333.
Cornillot, et al., The Genes for Butanol and Acetone Formation in Clostridium Acetobutylicum ATCC 824 Reside on a Large Plasmid Whose Loss Leads to Degeneration of the Strain, Journal of Bacteriology, 1997, 179(17):5442-5447.
Finn, et al., The Structural Gene for Tetanus Neurotoxin is on a Plasmid, Science, 1984, 224(4651):881-884.
Hatheway, Chapter 1—Bacterial Sources of Clostridial Neurotoxins, "Botulinum Neurotoxin and Tetanus Toxin", Copyright 1989 Academic Press, Inc., pp. 3-24.
Hatheway, Toxigenic Clostridia, Clinical Microbiology Reviews, 1990, 3(1):66-98.
Hill, et al., Genetic Diversity Among Botulinum Neurotoxin-Producing Clostridial Strains, Journal of Bacteriology, 2007, 189(3):818-832.
Jankovic, et al., Therapeutic Uses of Botulinum Toxin, The New England Journal of Medicine, 1991, 324:1186-1194.
Johnson, et al., Clostridium Botulinum and its Neurotoxins: A Metabolic and Cellular Perspective, Toxicon, 2001, 39 (11):1703-1722.
Johnson, et al., Characterization of Clostridium Botulinum Strains Associated with an Infant Botulism Case in the United Kingdom, Journal of Clinical Microbiology, 2005, 43(6):2602-2607.
Johnson, Chapter 14—Bacteriophages Encoding Botulinum and Diphtheria Toxins, "Phages: Their Role in Bacterial Pathogenesis and Biotechnology", Copyright 2005 ASM Press, pp. 280-296.
Jovita, et al., Gene Organization and Sequence Determination of the Two Botulinum Neurotoxin Gene Clusters in Clostridium Botulinum Type A(B) Strain NCTC 2916, Current Microbiology, 1998, 36:226-231.
Marshall, et al., Plasmid Encoded Neurotoxin Genes in Clostridium Botulinum Serotype A Subtypes, Biochemical and Biophysical Research Communications, 2007, 361:49-54.
Ochman, Bacterial Evolution: Chromosome Arithmetic and Geometry, Current Biology, 2002, 12:R427-R428.
Rasko, et al., Complete Sequence Analysis of Novel Plasmids from Emetic and Periodontal Bacillus cereus Isolates Reveals a Common Evolutionary History Among the B. cereus-Group Plasmids, Including Bacillus anthracis pXO1, Journal of Bacteriology, 2007, 189(1):52-64.
Sambrook, et al., Molecular Cloning—A Laboratory Manual, Third Edition, Cold Spring Harbor Laboratory Press, 2001 [Title Page and Table of Contents Only].
Schantz, et al., Properties and Use of Botulinum Toxin and Other Microbial Neurotoxins in Medicine, Microbiological Reviews, 1992, 56(1):80-99.

(Continued)

*Primary Examiner* — Nashaat Nashed
(74) *Attorney, Agent, or Firm* — Quarles & Brady LLP (57) ABSTRACT

The present invention provides a novel isolated plasmid, wherein the plasmid is a native plasmid found in unique *C. botulinum* type A strains and encode either BoNT/A3 or BoNT/A4 and BoNT/B. The present invention also provides a method of obtaining a plasmid-encoded botulinum neurotoxin and botulinum neurotoxin complex comprising the step of isolating a plasmid encoding the cntA/A or cntA/B neurotoxin gene and genes encoding protein components of the toxin complex from a *C. botulinum* type A strain. The inventors performed comparative analyses of representative BoNT/A subtype strains by pulsed-field gel electrophoresis (PFGE) and Southern hybridizations with probes specific for the BoNT/A and B genes, cntA/A and cntA/B. Unexpectedly, the inventors determined that the genes encoding BoNT/A3 in the A3 strain, and BoNT/A4 and BoNT/B in the A4 strain, are on plasmids.

6 Claims, 5 Drawing Sheets

(56) References Cited

OTHER PUBLICATIONS

Sebaihia, et al., Genome Sequence of a Proteolytic (Group I) Clostridium Botulinum Strain Hall A and Comparative Analysis of the Clostridial Genomes, Genome Research, 2007, 17:1082-1092.

Smith, et al., Sequence Variation Within Botulinum Neurotoxin Serotypes Impacts Antibody Binding and Neutralization, Infection and Immunity, 2005, 73(9):5450-5457.

Smith, et al., Analysis of the Neurotoxin Complex Genes in Clostridium Botulinum A1-A4 and B1 Strains: BoNT/A3, /Ba4 and /B1 Clusters are Located within Plasmids, PLoS One, 2007, 12:E1271, pp. 1-10.

Strom, et al., Plasmids in Clostridium Botulinum and Related Clostridial Species, Applied and Environmental Microbiology, 1984, 48(5):956-963.

Weickert, et al., Production of Toxin by Clostridium Botulinum Type A Strains Cured of Plasmids, Applied and Environmental Microbiology, 1986, 51(1):52-56.

Zhou, et al., The Genes for the Clostridium Botulinum Type G Toxin Complex Are on a Plasmid, Infection and Immunity, 1995, 63(5):2087-2091.

PCT International Search Report and Written Opinion, PCT/US08/68532, Oct. 15, 2008.

Australian Government IP Australia, Examiner's First Report, Application No. 2008270020, Feb. 6, 2012.

Applicant, Response to Australian Government IP Australia Feb. 6, 2012 Examination Report, Application No. 2008270020, Feb. 1, 2013.

Australian Government IP Australia, Patent Examination Report No. 2, Application No. 2008270020, Feb. 25, 2013.

Applicant, Response to Australian Government IP Australia Feb. 25, 2013 Examination Report, Application No. 2008270020, Apr. 15, 2013.

Canadian Intellectual Property Office, Examination Report, Application No. 2,691,825, Sep. 6, 2013.

European Patent Office, Communication, Application No. EP 08772138, Jun. 11, 2012.

Applicant, Response to European Patent Office Jun. 11, 2012 Communication, Application No. EP 08772138, Oct. 18, 2012.

Intellectual Property Office of New Zealand, Examination Report, Application No. 582087, Nov. 8, 2010.

Applicant, Response to Intellectual Property Office of New Zealand Nov. 8, 2010, Examination Report, Application No. 582087, Mar. 7, 2012.

Intellectual Property Office of New Zealand, Examination Report, Application No. 582087, Mar. 26, 2012.

Applicant, Response to Intellectual Property Office of New Zealand Mar. 26, 2012, Examination Report, Application No. 582087, May 23, 2012.

Hatheway, et al. "Atypical Toxin Variant of Clostridium botulinum Type B Associated with Infant Botulism" J. Clin. Microbiol., Dec. 1981, pp. 607-611, vol. 14, No. 6.

Marshall, et al. "Plasmid encoded nerotoxin genes in Clostridium botulinum" Biochem. & Biophys. Res. Comm., Jul. 2007, pp. 49-54, vol. 361.

Smith, et al. "Analysis of the Neurotoxin Complex Genes in Clostridium botulinium A1-A4 and B1 Strains: BoNT/A3, /Ba4 and /B1 Clusters Are Located within Plasmids" PLoS One, Dec. 2007, pp. 1-10, vol. 2, Issue 12.

Edmond, et al. "Case of infant botulism in Texas" Texas Medicine, pp. 85-88, Oct. 1977, vol. 73.

```
SEQUENCE LISTING

<160> NUMBER OF SEQ ID NOS: 6

<210> SEQ ID NO 1
<211> LENGTH: 25
<212> TYPE: DNA
<213> ORGANISM: ARTIFICIAL
<220> FEATURE:
<223> OTHER INFORMATION: SYNTHETIC NUCLEOTIDE-PCR PRIMER

<400> SEQUENCE: 1
gctactaatg catcacaggc aggcg                                           25

<210> SEQ ID NO 2
<211> LENGTH: 21
<212> TYPE: DNA
<213> ORGANISM: ARTIFICIAL
<220> FEATURE:
<223> OTHER INFORMATION: SYNTHETIC NUCLEOTIDE-PCR PRIMER

<400> SEQUENCE: 2
cccatgagca acccaaagtc c                                               21

<210> SEQ ID NO 3
<211> LENGTH: 22
<212> TYPE: DNA
<213> ORGANISM: ARTIFICIAL
<220> FEATURE:
<223> OTHER INFORMATION: SYNTHETIC NUCLEOTIDE-PCR PRIMER

<400> SEQUENCE: 3
tttgcatcaa gggaaggctt cg                                              22

<210> SEQ ID NO 4
<211> LENGTH: 20
```

```
<212> TYPE: DNA
<213> ORGANISM: ARTIFICIAL
<220> FEATURE:
<223> OTHER INFORMATION: SYNTHETIC NUCLEOTIDE-PCR PRIMER

<400> SEQUENCE: 4
aggaatcact aaaataagaa                                            20

<210> SEQ ID NO 5
<211> LENGTH: 20
<212> TYPE: DNA
<213> ORGANISM: ARTIFICIAL
<220> FEATURE:
<223> OTHER INFORMATION: SYNTHETIC NUCLEOTIDE-PCR PRIMER

<400> SEQUENCE: 5
gcggcgtgcc taacacatgc                                            20

<210> SEQ ID NO 6
<211> LENGTH: 20
<212> TYPE: DNA
<213> ORGANISM: ARTIFICIAL
<220> FEATURE:
<223> OTHER INFORMATION: SYNTHETIC NUCLEOTIDE-PCR PRIMER

<400> SEQUENCE: 6
atctcacgac acgagctgac                                            20
```

PLASMID-ENCODED NEUROTOXIN GENES IN *CLOSTRIDIUM BOTULINUM* SEROTYPE A SUBTYPES

CROSS-REFERENCE TO RELATED APPLICATIONS

This application is a continuation of U.S. application Ser. No. 12/664,800, filed Jun. 30, 2010, which is a national stage application of PCT/US2008/68532, filed Jun. 27, 2008, which claims priority to U.S. Provisional Application No. 60/947,090, filed Jun. 29, 2007, all of which are hereby incorporated by reference herein in their entirety for all purposes.

STATEMENT REGARDING FEDERALLY-SPONSORED RESEARCH OR DEVELOPMENT

This invention was made with government support under AI056493 and AI065359 awarded by the National Institutes of Health. The government has certain rights in the invention.

FIELD OF THE INVENTION

This invention is directed to isolated plasmid encoding neurotoxin genes in *Clostridium botulinum* serotypes.

BACKGROUND OF THE INVENTION

*Clostridium botulinum* produces botulinum neurotoxin (BoNT), the causative agent of the debilitating disease botulism that affects humans and animals. BoNTs have also been considered as potential bioterrorism (BT) agents. For instance, in 2001 *C. botulinum* was listed as a category A select agent due to its potential use as a BT agent [1]. In addition to its importance as a pathogen and potential BT agent, BoNTs are now widely used as pharmaceuticals to treat a myriad of neuronal disorders.

Seven distinguishable serotypes of BoNT, designated A-G, are produced by *C. botulinum*. The serotypes are described as BoNT/A, BoNT/B, BoNT/C, etc. BoNTs are produced as progenitor toxin complexes in which the neurotoxin is associated with nontoxic components: nonhemagglutinin (NTNH), hemagglutinin (HA), other uncharacterized protein components, and nucleic acids [2]. The genes encoding the neurotoxin and associated protein components of the toxin complexes are organized in a cluster, and their location and composition varies among the different serotypes and strains [3]. For further information concerning the properties of the various *C. botulinum* toxins, reference is made to the article by Jankovic and Brin, The New England Journal of Medicine, No. 17, 1990, pp. 1186-1194, and to the review by Charles L. Hatheway in Chapter 1 of the book entitled Botulinum Neurotoxin and Tetanus Toxin, L. L. Simpson, Ed., published by Academic Press Inc. of San Diego, Calif., 1989, the disclosures in which are incorporated herein by reference.

The neurotoxic component of *C. botulinum* has a molecular weight of about 150 kilodaltons (kD) and is comprised of a polypeptide chain of about 50 kD (Lc) which is considered to be responsible for the toxic properties of the toxin (i.e., by interfering with the exocytosis of acetylcholine, by decreasing the frequency of acetylcholine release) and a larger polypeptide chain of about 100 kD (Hc), which is believed to be necessary to enable the toxin to bind to the pre-synaptic membrane and to enter into neurons. The neurotoxin gene clusters for *C. botulinum* serotypes A, B, E and F are believed to be located on the chromosome, while the neurotoxin gene clusters for *C. botulinum* serotypes C1 and D are carried on bacteriophages [4]. In *C. botulinum* BoNT/G, the neurotoxin gene (cntA/G) was shown to reside on a large plasmid of approximately 114 kb [5].

Four BoNT/A subtypes (A1-A4) have recently been identified [6, 7, 8]. Although BoNT/A subtypes exhibit a high degree of sequence conservation, variations in substrate recognition and receptor binding regions are sufficient to significantly affect efficient vaccine and countermeasure development [6, 8], as well as potentially affecting pharmaceutical activity. It has also been observed that different type A strains, even within the same subtype, produce varying quantities of BoNT [9]. For instance, experiments have determined that *C. botulinum* subtype A3 strain Loch Maree, and subtype A4 strain 657Ba, produce considerably less BoNT than most A1 and A2 subtype strains. Interestingly, the dual neurotoxin strain 657Ba produces primarily BoNT/B and even lower quantities of BoNT/A than the Loch Maree strain. This complicates purification of sufficient quantities of these proteins, as required for fundamental molecular biology and structural studies, as well as commercial and therapeutic uses of the proteins.

Therapeutic uses of BoNT include dystonias, chronic facial pain, strabismus, chronic headache, spastic muscle disorders, and other chronic ailments that require repeated administration of BoNT-complexes. Commercially available pharmaceuticals comprising BoNT-complexes (as distinct from purified neurotoxin), i.e., BOTOX (Allergan, Inc.) are serotype A1. Stereotype B has also been commercially marketed as NEUROBLOC or MYOBLOC (Solstice, Inc.), but is mainly used secondary to stereotype A because of the large number of Units required for treatment and its relatively short duration of action compared to serotype A, which has the longest duration of action compared to the other six serotypes of BoNT. Although it is the predominant currently approved type of BoNT, serotype A is immunogenic, meaning that people become resistant to it after repeated use. Accordingly, a need exists for a BoNT/A subtype that is not neutralized from antibodies present against BoNT/A1 after repeated use, an isolated and purified source thereof, as well as methods of obtaining and using said BoNT/A subtype.

SUMMARY OF THE INVENTION

The present invention provides a novel isolated plasmid, wherein the plasmid is a native plasmid found in a *C. botulinum* type A strain. In one embodiment the plasmid encodes BoNT/A3. In an alternate embodiment the plasmid encodes BoNT/A4 and BoNT/B. The *C. botulinum* type A strain is preferably selected from the group consisting of ATCC 3502 [subtype A1], 62A [subtype A1], KyotoF [subtype A2], 5328A [subtype A1/A2], Loch Maree [subtype A3] and similar or identical subtype A3 isolates obtained from culture collections and governmental agencies, 657Ba [subtype A4] and NCTC 2916 [subtype A(B)]. The plasmids harboring the gene for BoNTs in these strains range from approximately 60 to 280 kb.

In an alternate embodiment, the present invention also provides a method of obtaining a plasmid-encoded botulinum neurotoxin complex (BoNT-complex). The method comprises the step of isolating a plasmid encoding the cntA/A or cntA/B neurotoxin gene as well as the associated protein complexes from a *C. botulinum* type A strain. The *C.*

*botulinum* type A strain is preferably selected from the group consisting of ATCC 3502 [subtype A1], 62A [subtype A1], KyotoF [subtype A2], 5328A [subtype A1/A2], Loch Maree [subtype A3] and similar or identical strains, 657Ba [subtype A4] and NCTC 2916 [subtype A(B)]. In one embodiment the *C. botulinum* type A strains are other *C. botulinum* strains that produce BoNT/A3 and BoNT/A3-complexes from plasmid-encoded genes. In an alternative embodiment the *C. botulinum* type A strain is 657Ba or other Ba strains carrying BoNT genes from plasmids.

In another embodiment, the invention provides a novel method of producing botulinum neurotoxin comprising the steps of isolating a plasmid encoding the cntA/A or cntA/B gene and those genes encoding the protein complexes from a *C. botulinum* type A strain; and introducing the plasmid to into a *clostridium* bacteria wherein the BoNT or complex is produced. The *C. botulinum* type A strain is preferably selected from the group consisting of ATCC 3502 [subtype A1], 62A [subtype A1], KyotoF [subtype A2], 5328A [subtype A1/A2], Loch Maree [subtype A3] and related or identical strains from various sources, 657Ba [subtype A4] and NCTC 2916 [subtype A(B)].

The present invention offers multiple advantages over the prior art. For instance, the isolated plasmid and method of obtaining the isolated plasmid provide useful methods for procuring sufficient quantities of the purified neurotoxin for use in therapeutic and research applications. In addition, the isolated plasmid provides a BoNT/A-complex and BoNT subtype that is not neutralized by antibodies to BoNT/A1 after repeated use, increasing the therapeutic applications of the plasmid of the present invention.

While multiple embodiments are disclosed, still other embodiments of the present invention will become apparent to those skilled in the art from the following detailed description. As will be apparent, the invention is capable of modifications in various obvious aspects, all without departing from the spirit and scope of the present invention. Accordingly, the detailed descriptions are to be regarded as illustrative in nature and not restrictive.

BRIEF DESCRIPTION OF THE FIGURES

FIG. 2. PFGE and Southern hybridization analyses of *C. botulinum* type A subtypes. (A) PFGE of non-digested DNA of *C. botulinum* A subtypes. Southern hybridizations were performed with cntA/A probe (B), cntA/B probe (C), and 16S rRNA gene probe (D). Lanes: lambda ladder PFG markers (New England Biolabs) (Lane M), ATCC 3502 (Lane 1), 62A (Lane 2), Kyoto F (Lane 3), 5328A (Lane 4), Loch Maree (Lane 5), 657Ba (Lane 6), NCTC 2916 (Lane 7). PFGE conditions: pulse time 5-60 seconds, 6V/cm, at 14° C. for 27 h.

FIG. 5. Several transconjugant clones were selected for analysis by PFGE to confirm the conjugative transfer of pCLK*/pCLK/pCLK*. Visualization of the plasmids by PFGE was initially performed with amples of nondigested DNA of three donor strains (*C. botulinum* Loch Maree/pCLK*/pCLK/pCLK*) the recipient strain (*C. botulinum* LNTO1) and several transconjugant clones (FIG. 5A). It has been determined in our laboratory that *C. botulinum* strain 62A contains a plasmid of ~150 kb, which was observed in *C. botulinum* LNTO1 as expected (FIG. 5A), as well as in each of the transconjugant clones selected for analysis, and absent from the donor strains (FIG. 5A). Next, PFGE of SmaI digested DNA of the donor, recipient and transconjugant clones verified the conjugal transfer of pCLK* since the restriction digestion pattern of each of the tested transconjugant clones was identical to that of the recipient, *C. botulinum* LNTO1 (FIG. 5B). This is the first evidence of conjugal transfer of a virulent plasmid in *C. botulinum* and provides a probable mechanism for the widespread distribution of virulence plasmids in other *C. botulinum* strains. This experiment has been repeated and we have noticed a relatively low conjugal transfer frequency of (10-6 to 10-7 transconjugants per donor), yet comparable megaplasmid transfer frequencies are observed in other bacteria.

DETAILED DESCRIPTION OF THE INVENTION

The present invention provides a novel isolated plasmid, wherein the plasmid is a native plasmid found in a *C. botulinum* type A strain and encodes either BoNT/A3 or BoNT/A4 and BoNT/B. The present invention also provides a method of obtaining a plasmid-encoded botulinum neurotoxin complex or isolated botulinum neurotoxin comprising the step of isolating a plasmid encoding the cntA/A or cntA/B neurotoxin gene from a *C. botulinum* type A strain and expressing the genes encoding for BoNT/A3, BoNT/A4 and BoNT/B neurotoxins and associated proteins of the neurotoxin complexes. The neurotoxin complex and the neurotoxin are purified and formulated in a manner suitable for use, such as in pharmaceuticals or vaccine preparation.

I. IN GENERAL

In the specification and in the claims, the terms "including" and "comprising" are open-ended terms and should be interpreted to mean "including, but not limited to . . . ." These terms encompass the more restrictive terms "consisting essentially of" and "consisting of."

As used herein and in the appended claims, the singular forms "a", "an", and "the" include plural reference unless the context clearly dictates otherwise. As well, the terms "a" (or "an"), "one or more" and "at least one" can be used interchangeably herein. It is also to be noted that the terms "comprising", "including", "characterized by" and "having" can be used interchangeably.

Unless defined otherwise, all technical and scientific terms used herein have the same meanings as commonly understood by one of ordinary skill in the art to which this invention belongs. All publications and patents specifically mentioned herein are incorporated by reference in their entirety for all purposes including describing and disclosing the chemicals, instruments, statistical analyses and methodologies which are reported in the publications which might be used in connection with the invention. All references cited in this specification are to be taken as indicative of the level of skill in the art. Nothing herein is to be construed as an admission that the invention is not entitled to antedate such disclosure by virtue of prior invention.

II. THE INVENTION

The present invention provides a novel isolated plasmid, wherein the plasmid is a native plasmid found in a *C. botulinum* type A strain and encodes either BoNT/A3 (plasmid pCLK) or BoNT/A4 and BoNT/B (plasmid pCLJ) and the associated protein complexes. The present invention also provides a method of obtaining a plasmid-encoded BoNT comprising the step of isolating a plasmid encoding the cntA/A or cntA/B neurotoxin and genes encoding BoNT-complexes from a *C. botulinum* type A strain. The two plasmids pCLK and pCLJ, which encode the BoNT and BoNT-complex genes, are uniquely distinct plasmids and each is found in a separate *C. botulinum* strain.

The inventors performed comparative analyses of representative BoNT/A subtype strains by pulsed-field gel electrophoresis (PFGE) and Southern hybridizations with probes specific for the BoNT/A and B genes, cntA/A and cntA/B. Unexpectedly, the inventors determined that the genes encoding BoNT/A3 in the A3 strain, and BoNT/A4 and BoNT/B in the A4 strain, are on plasmids. This is the first demonstration of a plasmid-located gene for BoNT in *C. botulinum* type A strains. This is advantageous for many reasons, such as providing an increased utility for protein production.

In a first embodiment, the present invention provides a novel, isolated plasmid, wherein the plasmid is a native plasmid found in a *C. botulinum* type A strain and encodes either BoNT/A3 or BoNT/A4 and BoNT/B.

A native plasmid, pCLK, has been discovered in *C. botulinum* strain Loch Maree which encodes the BoNT/A3 gene, cntA/A3 (Marshall et al. 2007; Smith et al. 2007). A separate native plasmid, pCLJ, has also been discovered in *C. botulinum* strain 657Ba that harbors both the BoNT/A4 and BoNT/bvB genes, cntA/A4 and cntA/bvB (by stands for bivalent B). These plasmids share significant homology, but are two separate and distinct entities. The plasmid pCLK is 266,805 bp and the plasmid pCLJ is 270,346 bp. Although plasmids have been observed in *C. botulinum* strains ATCC 3502, 62A and 5328A the BoNT gene has not been found to be associated with these plasmids; instead BoNT/A is located on the chromosome in these strains (Marshall et al. 2007).

Figure 3:
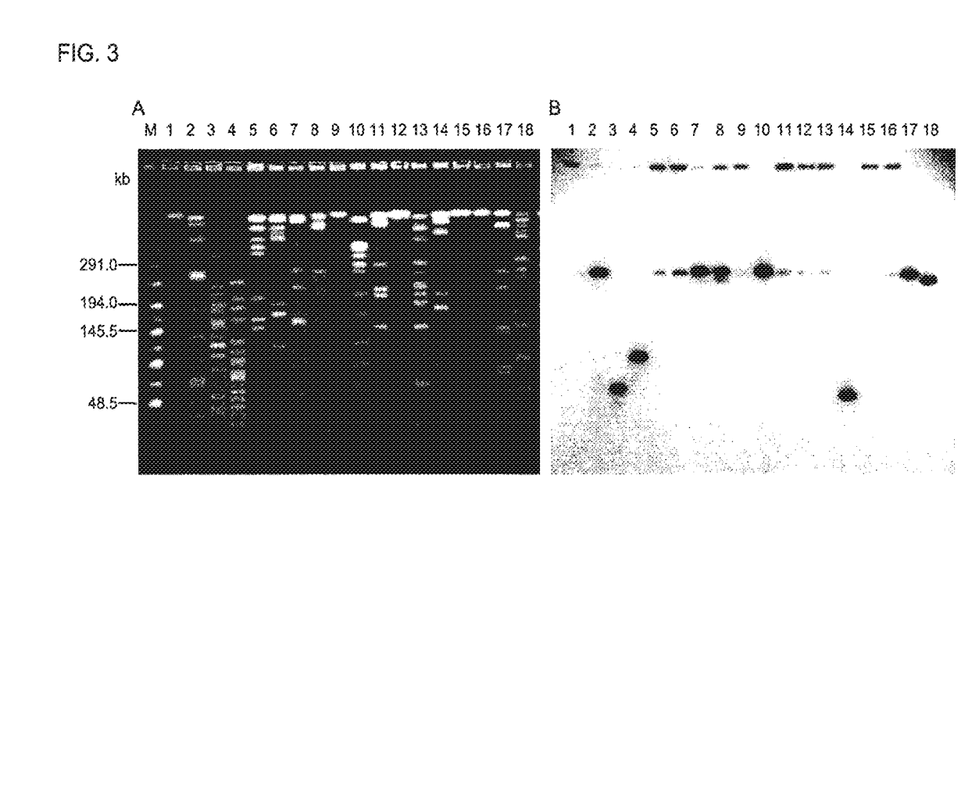
FIG. 3. PFGE and Southern hybridization analyses of digested DNA from *C. botulinum* strain Loch Maree. (A) PFGE of digested DNA of Loch Maree. (B) Southern hybridization of Loch Maree PFGE with the cntA/A probe. Lanes 1: Nondigested DNA, Digests with: 2-AatII, 3-ApaI, 4-BglII, 5-EagI, 6-MluI, 7-NaeI, 8-NarI, 9-NotI, 10-NruI, 11-PvuI, 12-RsrII, 13-SacII, 14-SalI, 15-SbfI, 16-SfiI, 17-SmaI, 18-XhoI; M-MidRange II PFG marker (New England Biolabs). PFGE conditions: pulse time 1-30 seconds, 6V/cm, at 14° C. for 24 h.
Figure 4:
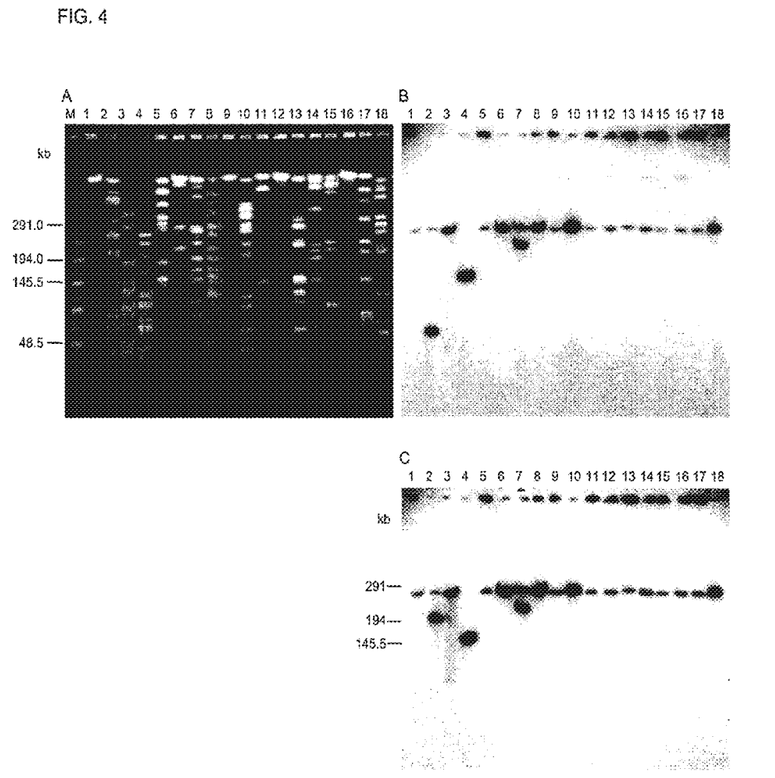
FIG. 4. PFGE and Southern hybridization analyses of digested DNA from *C. botulinum* strain 657Ba. (A) PFGE of digested DNA of 657Ba. (B) Southern hybridization of 657Ba PFGE with the cntA/A probe. (C) Southern hybridization of 657Ba PFGE with the cntA/B probe. Lanes 1-Nondigested DNA, Digests with: 2-AatII, 3-ApaI, 4-BglII, 5-EagI, 6-MluI, 7-NaeI, 8-NarI, 9-NotI, 10-NruI, 11-PvuI, 12-RsrII, 13-SacII, 14-SalI, 15-SbfI, 16-SfiI, 17-SmaI, 18-XhoI; M-MidRange II PFG marker (New England Biolabs). PFGE conditions: pulse time 1-30 seconds, 6V/cm, at 14° C. for 24 h.
Figure 5:
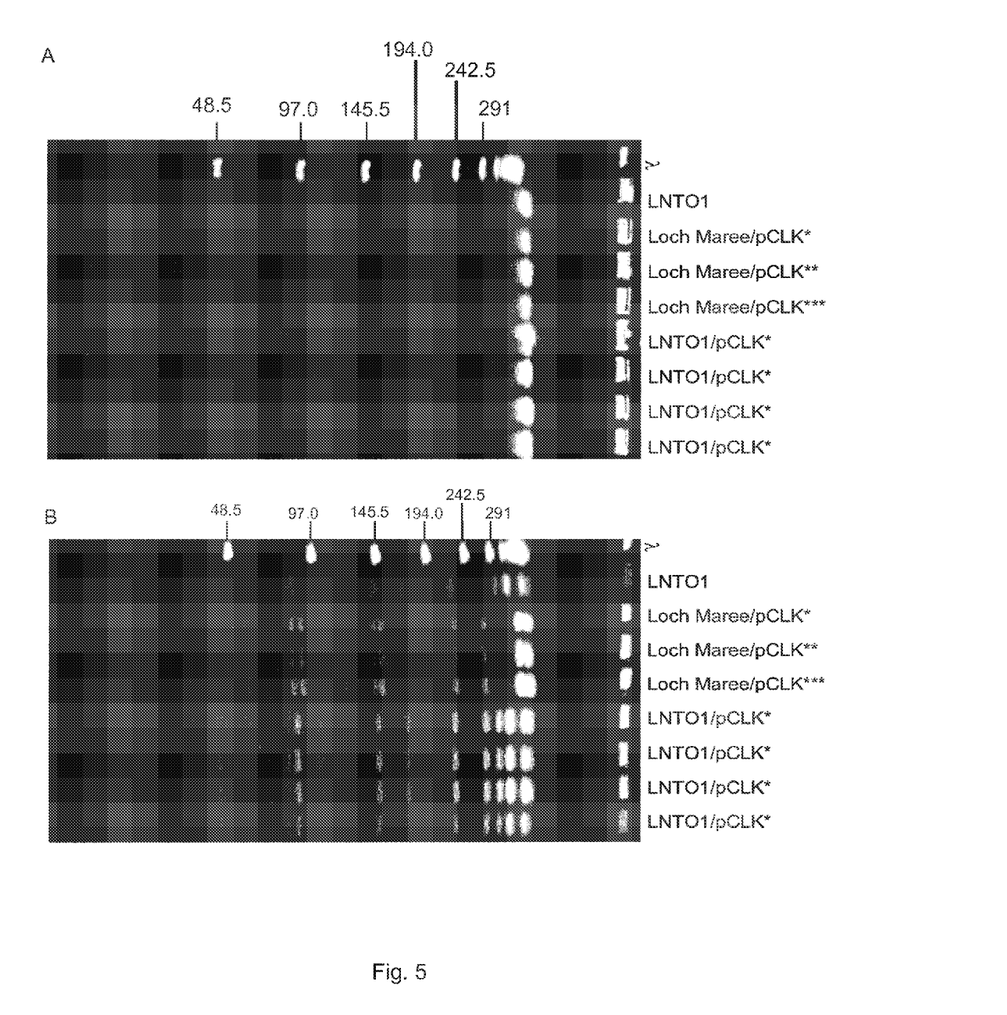

By "plasmid" we mean an autonomously replicating, extrachromosomal, circular DNA molecule, distinct from the normal bacterial genome and nonessential for cell survival under nonselective conditions. Some plasmids are capable of integrating into the host genome. A number of artificially constructed plasmids are used as cloning vectors. The plasmids of the present invention that possess genes encoding for BoNTs range in size from approximately 60 to 280 kb. The sizes of the plasmids that encode the neurotoxin genes as well as the toxin complex genes are 266,805 bp (pCLK, *C. botulinum* strain Loch Maree) and 270,346 bp (pCLJ, *C. botulinum* strain 657Ba). The inventors have shown that only pCLK of *C. botulinum* strain Loch Maree is capable of conjugal transfer (FIG. 5). Conjugal transfer of pCLK from *C. botulinum* Loch Maree to *C. botulinum* strain LNTO1 (A1 subtype strain) was demonstrated. *C. botulinum* strain LNTO1 is a transposon Tn916 nontoxigenic mutant of *C. botulinum* strain 62A (Johnson et al. 1997). Upon transposon insertion, *C. botulinum* LNTO1 has lost a 32.5 kb region containing the entire neurotoxin gene cluster and regions flanking the cluster. Tn916 is a tetracycline-encoded conjugative transposon and its presence in LNTO1 provides an excellent means for the selection for transconjugants. As described in the Examples below, the plasmid(s) can be located using restriction analysis and Southern hybridization (FIGS. 3 and 4).

By "isolated" we mean a plasmid that is identified and separated from at least one component or contaminant with which it is ordinarily associated in its natural source. An isolated plasmid is present in a form or setting that is different from that in which it is found in nature. In contrast, non-isolated plasmids are found in the state they exist in nature. The plasmids of the present invention may be isolated by any known method of isolating plasmids found in bacteria. One of skill in molecular biology will understand that there are numerous suitable methods for isolating large plasmids found in bacteria known in the art [5, 20, 21].

By a "*C. botulinum* type A strain" we mean a type A strain known to the art, including but not limited to those strains selected from the group consisting of ATCC 3502 [subtype A1], 62A [subtype A1], KyotoF [subtype A2], 5328A [subtype A1/A2], Loch Maree (GenBank Accession No. ABA29017) [subtype A3], 657Ba (GenBank Accession No. ABA29018) [subtype A4] and NCTC 2916 [subtype A(B)]. In a preferred embodiment the type A strain is a type A3 strain such as Loch Maree or a type A4 strain such as 657Ba. Other A3 and A4 strains that contain plasmids containing neurotoxin gene clusters are also envisioned as acceptable for this invention.

In a second embodiment, the present invention provides a novel method of obtaining a plasmid-encoded botulinum neurotoxin and neurotoxin protein complex. The method comprises the step of isolating a plasmid encoding the cntA/A or cntA/B neurotoxin genes and genes for the complex proteins from a *C. botulinum* type A strain. In a preferred method the *C. botulinum* type A strain is selected from the group consisting of ATCC 3502 [subtype A1], 62A [subtype A1], KyotoF [subtype A2], 5328A [subtype A1/A2], Loch Maree [subtype A3], 657Ba [subtype A4] and NCTC 2916 [subtype A(B)]. In a preferred embodiment the type A strain is a type A3 strain such as Loch Maree or a type A4 strain such as 657Ba. Other A3 and A4 strains that contain plasmids containing neurotoxin gene clusters are also envisioned as acceptable for this invention.

The plasmid may be isolated by any known method of isolating plasmids found in bacteria. One of skill in molecular biology will understand that there are numerous suitable methods for isolating large plasmids found in bacteria known in the art [5, 20, 21].

In a third embodiment, the present invention provides methods of producing botulinum neurotoxin and their proteins complexes. In one embodiment, the isolated plasmid of the present invention may be modified to increase protein production. In particular, one may wish to manufacture proteins in clostridia. The isolated plasmids of the present invention may also be useful for genetic manipulations in *Clostridium* species.

III. EXAMPLES

The following examples are, of course, offered for illustrative purposes only, and are not intended to limit the scope of the present invention in any way. Indeed, various modifications of the invention in addition to those shown and described herein will become apparent to those skilled in the art from the foregoing description and the following examples and fall within the scope of the appended claims.

Bacterial strains. The following *C. botulinum* type A subtype strains from the inventors laboratory culture collection were used: ATCC 3502 [subtype A1], 62A [subtype A1], KyotoF [subtype A2], 5328A [subtype A1/A2], Loch Maree (GenBank Accession No. ABA29017) [subtype A3], 657Ba (GenBank Accession No. ABA29018) [subtype A4] and NCTC 2916 [subtype A(B)]. All cultures were maintained as frozen stocks at −80° C. in TPGY (50 g/liter trypticase peptone, 5 g/liter Bacto peptone, 4 g/liter D-glucose, 20 g/liter yeast extract, 1 g/liter cysteine-HCl, pH 7.4) broth supplemented with 40% glycerol. All bacterial media components and chemicals were purchased from Becton Dickinson Microbiology Systems, Sparks, Md. and Sigma-Aldrich, St. Louis, Mo.

Preparation of agarose plugs for PFGE analysis. Bacterial cultures were grown anaerobically, PFGE plugs prepared, and PFGE performed as previously described [10].

Southern Hybridization. Type A neurotoxin gene sequences of all four *C. botulinum* type A subtype strains [6] were aligned and primers were designed to anneal to a conserved region of the C-terminal trefoil subdomain in the binding domain of the heavy chain. The forward primer: 5'GCTACTAATGCATCACAGGCAGGCG3' (SEQ ID NO: 1) and reverse primer: 5'CCCATGAGCAACCCAAAGTCC3' (SEQ ID NO: 2) were used in PCR amplification to generate a 268 bp DNA probe for cntA/A. A portion of the light chain of cntA/B was PCR amplified from the genomic DNA of *C. botulinum* strain 657Ba to generate a fragment of 592 bp using: forward primer: 5'TTTGCATCAAGGGAAGGCTTCG3' (SEQ ID NO: 3) and reverse primer: 5'AGGAATCACTAAAATAAGAA3' (SEQ ID NO: 4). A 16S rDNA probe for *C. botulinum* type A was amplified by PCR using genomic DNA from an A1 subtype strain as a template to yield a DNA fragment of 1020 bp using primers: forward primer: 5'GCGGCGTGCCTAACACATGC3' (SEQ ID NO: 5) and reverse primer: 5'ATCTCACGACACGAGCTGAC3' (SEQ ID NO: 6).

The PCR products were purified from agarose gels using Qiagen extraction kit (Qiagen, Valencia, Calif.), and were radioactively labeled with 32P using the Megaprime DNA labeling system (GE Healthcare Bio-Sciences, Piscataway, N.J.). The DNA samples separated by PFGE were transferred to a positively charged nylon membrane (Immobilon-NY+, Millipore, Bedford, Mass.) overnight by downward capillary transfer in 0.4 M NaOH, 1.5 M NaCl. The membranes were neutralized in 2 M Tris-HCl, pH 7.0 for 10 minutes, rinsed with 2×SSC and fixed at 80° C. for 30 minutes under vacuum. Hybridization was performed at 42° C. for 16 hours in a solution containing 5×Denhardt, 6×SSC, 50% formamide, 1% SDS, 100 μg/ml herring sperm DNA (Promega, Madison, Wis.) and 32P-labeled probes.

All hybridization solutions and buffers were prepared according to standard protocols [11]. After hybridizations the membranes were washed twice for 5 minutes each at room temperature with 2×SSC, 0.1% SDS and twice for 15 minutes each at 42° C. The membranes hybridized with the ribosomal probe were washed twice for 27 hours each at 65° C. with 0.1×SSC, 0.1% SDS. Autoradiography of the membranes was performed for 16 to 48 hours at −70° C. using Kodak BioMax MS film with a BioMax intensifying screen (Eastman Kodak, Rochester, N.Y.).

Bacteriophage Induction. Bacterial cultures of *C. botulinum* strains Loch Maree (subtype A3) and 657Ba (subtype A4) were grown anaerobically at 37° C. in 10 ml tubes of TPGY media to an OD600 of 0.2. Mitomycin C at a final concentration of 5 μg/ml was added to the cultures to induce cell lysis. The cultures were further incubated at 37° C. for 4-6 hours or until lysis was complete. The OD600 of the cultures was measured at 1 hour intervals. When lysis was complete the cultures were cooled to room temperature and bacteriophage particles were isolated following a standard protocol [11]. Bacteriophage particles were embedded in agarose plugs, treated as described above, and subjected to PFGE analysis and Southern hybridization.

Results and Discussion. *C. botulinum* strains Loch Maree and 657Ba produce very low quantities of BoNT/A3 and BoNT/A4, respectively, compared to other BoNT/A strains (unpublished data). Therefore, purification of sufficient quantities of these neurotoxins required for development of therapeutics and countermeasures is obstructed. Evaluating the genetic location of the neurotoxin genes in these strains could impact the levels of BoNTs. Previous studies have observed significant variations in growth patterns and BoNT production levels among different *C. botulinum* serotypes and even between strains within the same serotype [9]. Kinetic studies of *C. botulinum* type A1 and A2 strains showed a temporal regulation of BoNT production that begins during late log and early stationary phase [9]. Neurotoxin production differed between the strains and was found to be primarily dependent on nutritional factors, cell lysis, and sporulation [3, 9].

In typical A1 and A2 subtype strains, neurotoxin expression and the formation of the progenitor toxin complex increased upon prolonged incubation reaching maximum quantities at 96 hours. *C. botulinum* strains Loch Maree and 657Ba showed no increase in the levels of neurotoxin produced after 24 hours, and consistent quantities were rarely detected between different batch cultures (data not shown). The neurotoxin gene clusters in *C. botulinum* serotypes C and D are carried by bacteriophages [4].

Figure 1:
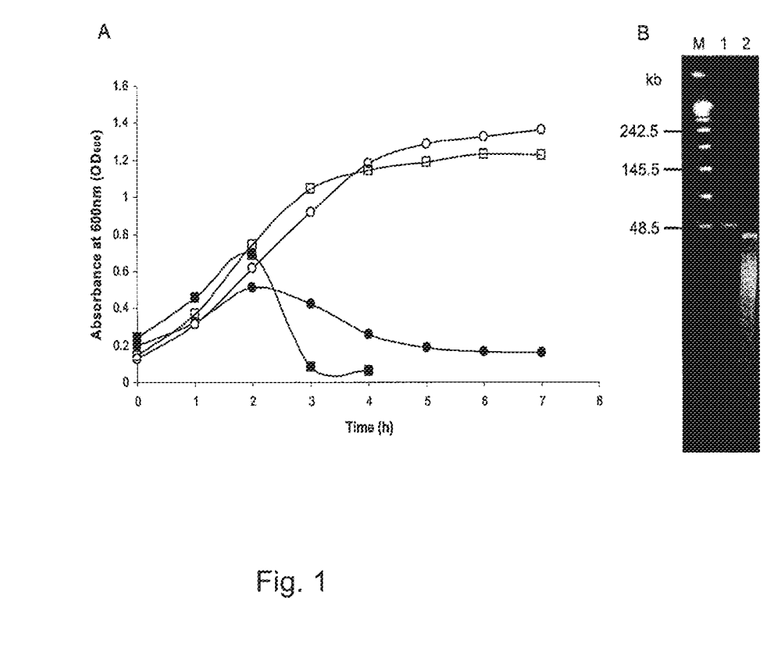
FIG. 1. Induction of bacteriophages in *C. botulinum* strains Loch Maree and 657Ba and PFGE analysis of phage DNA. (A) Lysis curve of strains Loch Maree and 657Ba after induction with mitomycin C (5 µg/ml) added at an OD600 of 0.2. (B) PFGE analysis of bacteriophage DNA isolated from strains Loch Maree (lane 1) and 657Ba (lane 2). Lambda Ladder PFG Marker (New England Biolabs) (Lane M). PFGE conditions: pulse time 1-20 seconds, 6V/cm, at 14° C. for 16 h. Loch Maree (circle), 657Ba (square) grown in TPGY without mitomycin C (open) and with mitomycin C (closed).

The bacteriophage carrier state in these serotypes has been termed pseudolysogeny because of the unstable nature of the prophage-bacterium relationship in which the prophage is often lost resulting in a nontoxigenic state [4]. The inventors hypothesized that a similar pseudolysogenic state may be responsible for the inconsistent production of BoNTs in strains Loch Maree and 657Ba. To test this hypothesis, bacterial cultures were treated with mitomycin C and bacteriophage particles were isolated from the culture lysates. Upon induction, the *C. botulinum* strain Loch Maree displayed a typical lysis pattern achieving complete lysis after six hours (FIG. 1A). In contrast, the *C. botulinum* strain 657Ba displayed a much faster lysis which was complete after only three hours (FIG. 1A).

PFGE analysis revealed a DNA band of 48.5 kb in the bacteriophage DNA preparations from both strains (FIG.

1B). A second DNA band of approximately 24 kb was also visible in the bacteriophage DNA preparation from strain 657Ba. Significant degradation of the bacteriophage DNA preparation from strain 657Ba seen in FIG. 1B was most likely due to the presence of high levels of endogenous proteinases and DNases released during rapid lysis of this particular strain upon bacteriophage induction. To test whether these bacteriophages harbor the neurotoxin gene, Southern hybridization with a cntA/A probe was conducted. No hybridization signals were observed with the bacteriophage DNAs (data not shown), indicating that the bacteriophage particles isolated from these strains do not carry the type A neurotoxin gene. The bacteriophages isolated from strains Loch Maree and 657Ba upon mitomycin C induction may contribute indirectly to the regulation, synthesis and release of neurotoxin.

The neurotoxins among the four BoNT/A subtypes show 84 to 93% identity [6]. The organization and composition of genes within the neurotoxin gene clusters also differ among the subtypes [3]. Presently, the nucleotide sequence of the entire genome has been determined for only one *C. botulinum* strain, ATCC 3502 [12], therefore the extent of sequence variation at the genome level between different subtype strains is not known.

To compare the genomes of representative *C. botulinum* strains producing BoNT/A1-A4 neurotoxins, PFGE and Southern hybridization analyses with neurotoxin gene specific probes were performed. In clostridia, preparation of high quality DNA plugs for PFGE analysis is challenging and some strains cannot be readily typed because they contain very high levels of endogenous DNases [3, 10]. To minimize the nucleolytic degradation of DNA samples, bacterial cultures were fixed with formaldehyde [10]. Typically, PFGE is performed with DNA samples that have been digested with rare cutting restriction endonucleases (RE), but to verify the quality of the DNA prior to restriction analysis, nondigested samples were first analyzed.

Figure 2:
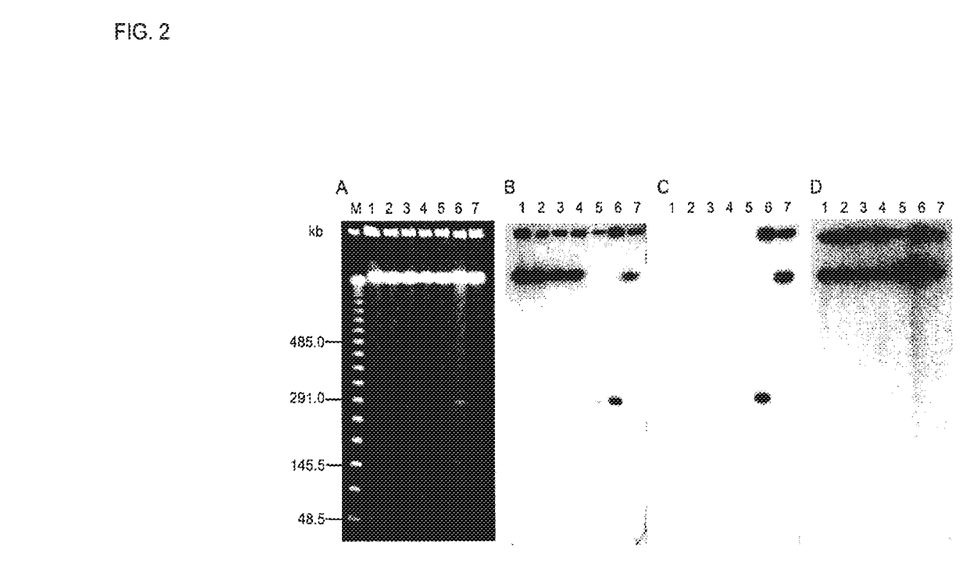

The inventors observed that a significant portion of DNA remained in the wells of the gel, representing intact chromosomal DNA. However, a portion of chromosomal DNA migrated a short distance into the gel, most likely corresponding to sheared DNA due to DNase activity (FIG. 2). Interestingly, several faint DNA bands that migrated beneath the sheared chromosomal DNA in strains 62A, 5328A, Loch Maree, and 657Ba were also observed (FIG. 2A), suggesting the presence of large extrachromosomal DNA elements. The extrachromosomal DNA molecules in strains Loch Maree and 657Ba migrated at a similar size at approximately 280 kb, while the DNA band in strain 657Ba was slightly larger (FIG. 2A). This band also appeared to be present at a higher copy number due to the increased intensity of the band observed in the ethidium bromide stained gel, as well as by stronger hybridization signals in the Southern blot (FIGS. 2A, B). In subsequent studies, considerable diversity in plasmid sizes have been indicated ranging from ca. 60 to 280 kb.

It has been determined that supercoiled plasmids migrate independently of the pulse time in PFGE, but large circular DNA molecules that are nicked or enzymatically relaxed fail to enter the gel matrix [13]. To verify the nature of these extrachromosomal elements, PFGE of nondigested DNA of these strains was performed several times employing different pulse times (data not shown). However, these extrachromosomal DNA molecules consistently migrated through the gels at the same size relative to the marker bands, suggesting that these bands may correspond to linear DNA plasmids. Cryptic plasmids ranging in size from 3 kb to 125 kb have been isolated from all *C. botulinum* serotypes but is strain dependent [14]. *C. botulinum* type G is the only serotype to date known to harbor a large plasmid (114 kb), which contains the BoNT/G gene cluster [5].

*Clostridium tetani* also carries a large plasmid (74 kb) possessing the tetanus neurotoxin (TeNT) gene [15]. It has been assumed that the neurotoxin gene clusters in *C. botulinum* serotypes A, B, E and F are located on the chromosomes. This has been confirmed for *C. botulinum* serotype A (subtype A1) through sequencing of the genome of the strain ATCC 3502 [12]. Prior to the present study, plasmids larger than that occurring in *C. botulinum* type G have not been identified in neurotoxigenic clostridia. The solventogenic *Clostridium acetobuytlicum* contains a megaplasmid (210 kb) which carries solventogenic genes encoding proteins involved in the production of acetone and butanol [16].

The finding of large extrachromosomal elements in *C. botulinum* type A strains 62A, 5328A, Loch Maree and 657Ba, prompted the inventors to investigate in more detail their potential role in neurotoxin production. Southern hybridizations were performed using probes specific for cntA/A, and cntA/B first using nondigested DNA samples (FIGS. 2B and C). Southern hybridization of the PFGE of nondigested DNA with the cntA/A probe produced strong signals at the well position, containing genomic and circular DNA, as well as with the band of sheared chromosomal DNA in all strains except Loch Maree and 657Ba (FIG. 2B). In these strains the cntA/A probe hybridized to DNA at the well position, but not with the sheared chromosomal DNA (FIG. 2B). Surprisingly, hybridization of cntA/A probe with the DNA bands at ~280 kb were observed for Loch Maree and 657Ba strains, indicating that the toxin gene is located on these extrachromosomal DNA molecules (FIG. 2B). The extrachromosomal DNA bands in strains 62A and 5328A did not hybridize with the cntA/A probe.

*C. botulinum* NCTC 2916 is an A(B) strain that produces active BoNT/A and carries a silent, unexpressed type B toxin gene cluster that is likely located on the chromosome [17]. Hybridization of cntA/B with the DNA of NCTC 2916 revealed strong signals at the level of sheared chromosomal DNA and at the well position supporting the location of cntA/B on the chromosome in this strain (FIG. 2C). Unexpectedly, in strain 657Ba, the cntA/B probe hybridized with the ~280 kb DNA band as well as with DNA at the well position (FIG. 2C). The presence of both neurotoxin gene clusters on the same plasmid was intriguing, because the location of cntA/B in the dual neurotoxin strain, 657Ba, was previously assumed to be on the chromosome.

To provide further evidence that the ~280 kb DNA elements in *C. botulinum* strains Loch Maree and 657Ba are plasmids and not sheared fragments of genomic DNA, the inventors also performed Southern hybridization of the nondigested DNA using a probe specific for 16S rDNA. Ribosomal DNA is specific to chromosomes and rarely found on plasmids [18]. Only sheared chromosomal DNA and DNA that remained at the well position hybridized with the 16S rDNA probe in all strains (FIG. 2D), no hybridization signals were observed with the extrachromosomal DNA bands. This supported that the DNA elements in these strains are plasmids.

To confirm the presence of cntA/A and cntA/B genes on these extrachromosomal DNA molecules in strains Loch Maree and 657Ba, seventeen rare cutting RE were chosen for the restriction analysis and Southern hybridizations of DNA preparations from these strains (FIGS. 3, 4). The majority of the RE chosen to digest the DNA of strains Loch Maree and 657Ba resulted in the same hybridization signals with uncut DNA, indicating that these enzymes did not cleave the plasmids (FIGS. 3B, 4B, C). However, digests with five RE in both strains showed an increase in the intensity of the ~280 kb band in the ethidium bromide stained gels as well as produced stronger hybridization signals with the toxin gene probes, while the hybridization signals at the well positions decreased (FIGS. 3B, 4B and 4C). This suggests that the plasmids were linearized by these REs and thus were able to enter and migrate through the gels at ~280 kb.

Four additional REs apparently cleaved the plasmid more than once in strain Loch Maree because hybridization signals were observed with DNA bands smaller than ~280 kb (FIG. 3). Similarly, three REs also cut the plasmid in strain 657Ba more than once (FIG. 4). Although the cntA/A and cntA/B genes are both present on the plasmid in 657Ba, they were found to be located on different areas of the DNA element as observed by the Southern hybridizations of DNA digested with the RE AatII (FIGS. 4B and 4C).

Plasmids from several *C. botulinum* type A strains have been isolated, but none of the plasmids have been associated with neurotoxin production [19]. This is the first demonstration that cntA/A, and cntA/B genes are located on a large plasmid (~280 kb) in type A neurotoxin producing *C. botulinum* strains. This finding has important implications for the evolution and pathogenicity of *C. botulinum*, including acquisition and expression of the toxins, and lateral transfer of toxin genes to nonpathogenic bacteria. As mentioned above, BoNT-encoding plasmids have also been obtained that very considerably in size from 60 to 280 kb.

REFERENCES

[1] Arnon et al., JAMA. 285 (2001) 1059-1081.
[2] Schantz et al., Microbiol. Rev. 56 (1992) 80-99.
[3] Johnson et al., Toxicon 39 (2001) 1703-1722.
[4] Johnson et al., Phages: Their Role in Bacterial Pathogenesis and Biotechnology, ASM Press, Washington, D.C., 2005, pp. 280-296.
[5] Zhou et al., Infect. Immun. 63 (1995) 2087-2091.
[6] Arndt et al., J. Mol. Biol. 362 (2006) 733-742.
[7] Hill et al., J. Bacteriol. 189 (2007) 818-237.
[8] Smith et al., Infect. Immun. 73 (2005) 5450-5457.
[9] Bradshaw et al., Anaerobe. 10 (2004) 321-333.
[10] Johnson et al., J. Clin. Microbiol. 43 (2005) 2602-2607.
[11] Sambrook, D. W. Russell, Molecular Cloning—A Laboratory Manual, third ed., Cold Spring Harbor Laboratory Press, Cold Spring Harbor, N.Y., 2001.
[12] Sebaihia et al., Genome Res. 2007 (epub ahead of print) 1-11.
[13] Beverly, Nucleic Acids Res. 16 (1988) 925-939.
[14] Strom et al., Appl. Environ. Microbiol. 48 (1984) 956-963.
[15] Finn et al., Science. 224 (1984) 881-884.
[16] Cornillot et al., J. Bacteriol. 179 (1997) 5442-5447.
[17] Rodriguez et al., Curr. Microbiol. 36 (1998) 226-231.
[18] Ochman et al., Curr. Biol. 12 (2002) R427-R428.
[19] Weickert et al., Appl. Environ. Microbiol. 51 (1986) 52-56.
[20] Johnson et al., J. Mol Biol, 362 (2006) 733-742.
[21] Rasko et al., J. Bacteriol. 189 (2007) 52-64.

We claim:

1. A method of obtaining a plasmid-encoded botulinum neurotoxin comprising the steps of:
    obtaining a bacterial strain comprising a plasmid-encoded botulinum neurotoxin type A,
    identifying a plasmid encoding the cntA/A or cntA/B gene from the bacterial strain, wherein (a) the cntA/A or cntA/B gene encodes BoNT/A3, and the bacterial strain is *Clostridium botulinum* type A strain Loch Maree; or (b) the cntA/A or cntA/B gene encodes BoNT/A4 and BoNT/B5, and the bacterial strain is *Clostridium botulinum* type A strain 657Ba;
    separating and purifying the plasmid encoding the cntA/A or cntA/B gene from the *Clostridium botulinum* type A strain; and
    introducing the plasmid into a *clostridium* bacteria and culturing the *Clostridium* bacteria, whereby a plasmid-encoded botulinum neurotoxin is obtained.

2. The method of claim 1 wherein the *Clostridium botulinum* type A strain is Loch Maree.

3. The method of claim 1 wherein the *Clostridium botulinum* type A strain is 657Ba.

4. A method of producing botulinum neurotoxins and botulinum neurotoxin complexes comprising the steps of:
    a) isolating a plasmid encoding the cntA/A or cntA/B gene from a *Clostridium botulinum* type A strain, wherein (a) the cntA/A or cntA/B gene encodes BoNT/A3, and the *Clostridium botulinum* type A strain is Loch Maree; or (b) the cntA/A or cntA/B gene encodes BoNT/A4 and BoNT/B5, and the *Clostridium botulinum* type A strain is 657Ba;
    b) separating and purifying the plasmid encoding the cntA/A or cntA/B gene from the *Clostridium botulinum* type A strain;
    c) introducing the plasmid into *clostridium* bacteria; and
    d) culturing the *clostridium* bacteria wherein the botulinum toxin complex and neurotoxins are produced and purified.

5. The method of claim 4 wherein the *Clostridium botulinum* type A strain is Loch Maree.

6. The method of claim 4 wherein the *Clostridium botulinum* type A strain is 657Ba.

* * * * *

UNITED STATES PATENT AND TRADEMARK OFFICE
CERTIFICATE OF CORRECTION

PATENT NO. : 9,453,057 B2
APPLICATION NO. : 13/800997
DATED : September 27, 2016
INVENTOR(S) : Johnson et al.

Page 1 of 1

It is certified that error appears in the above-identified patent and that said Letters Patent is hereby corrected as shown below:

In the Specification

Column 5, Line 56 - "by stands for" should be -- bv stands for --

Signed and Sealed this
Sixth Day of March, 2018

Andrei Iancu
*Director of the United States Patent and Trademark Office*